United States Patent [19]
Nigam

[11] Patent Number: 6,007,510
[45] Date of Patent: Dec. 28, 1999

[54] IMPLANTABLE DEVICES AND METHODS FOR CONTROLLING THE FLOW OF FLUIDS WITHIN THE BODY

[75] Inventor: Alok Nigam, Trabuco Canyon, Calif.

[73] Assignee: Anamed, Inc., Irvine, Calif.

[21] Appl. No.: 08/738,332

[22] Filed: Oct. 25, 1996

[51] Int. Cl.⁶ ..................................................... A61M 5/00
[52] U.S. Cl. ............................... 604/8; 604/9; 604/892.1
[58] Field of Search ........................... 604/8, 9, 93, 133, 604/247, 294, 890.1–892.1; 623/9

[56] References Cited

U.S. PATENT DOCUMENTS

| | | | |
|---|---|---|---|
| 4,037,604 | 7/1977 | Newkirk | 604/9 |
| 5,345,464 | 9/1994 | Camras | 604/9 |
| 5,385,582 | 1/1995 | Ommaya | 604/890.1 X |

*Primary Examiner*—Ronald Stright
*Assistant Examiner*—A. T. Nguyen
*Attorney, Agent, or Firm*—Stout, Uxa, Buyan & Mullins, L.L.P.

[57] ABSTRACT

Implantable fluid shunting devices and associated methods for controlling the pressure of fluids within anatomical spaces or cavities of the body. The device generally comprises a tube having a diffusion barrier (e.g., diffusion chamber) formed on a proximal end thereof. Fluid which flows through the tube will collect within the diffusion chamber and will diffuse outwardly therethrough. However, the presence of the diffusion chamber will prevent microbes, cells or other matter from interfering with or backflowing through the tube. Additionally, the tube may be provided with a pressure-openable aperture through which fluid from the tube may flow into the diffusion chamber. Such pressure-openable aperture will remain closed, until the pressure of fluid within the tube exceeds a predetermined maximum pressure $P_{MAX}$. In this manner, the pressure-openable aperture will limit the amount of fluid drained from the anatomical space or cavity of the body, thereby avoiding hypotony within such anatomical space or cavity.

14 Claims, 4 Drawing Sheets

IMPLANTABLE DEVICES AND METHODS FOR CONTROLLING THE FLOW OF FLUIDS WITHIN THE BODY

FIELD OF THE INVENTION

The present invention relates generally to medical apparatus and methods, and more particularly to a device which is implantable in a mammalian body to control the pressure of fluid within a body cavity by shunting such fluid to another site within the body, when the fluid pressure within the body cavity reaches a pre-determined level.

BACKGROUND OF THE INVENTION

A number of diseases and disorders in humans and other mammals are characterized by the build-up of excessive fluid pressure within one or more body cavities. In many instances, implantable devices or surgical procedures may be used to shunt excessive fluid from the body cavity wherein the excessive pressure build up is present, to one or more other sites within the body, as a means of receiving the undesirable pressure buildup, and thereby deterring the development of undesirable sequelae which may result from such pressure build-up.

i. Glaucoma

Glaucoma is a disease of the eye which is characterized by high intraocular pressure, and is among the leading causes of blindness in the world. In general, glaucoma results from a defect in the functional drainage system, whereby naturally occurring endogenous fluid (e.g., aqueous humor) is drained from the interior of the eye. The result of this decreased functional drainage of the eye is three-fold: a) increased intraocular pressure, b) degeneration of the optic nerve and supporting tissue at the optic nerve head (disk), and c) progressive loss of the visual field.

Individual cases of glaucoma are generally classified, on the basis of etiology, into two categories. These two major are "closed angle glaucoma" and "open angle glaucoma".

In closed angle glaucoma (syn. "angle-closure glaucoma", "narrow-angle glaucoma", "pupillary block glaucoma") excessive fluid accumulates within the anterior chamber of the eye due to the gradual closure of an anterior angle formed by the junction of the iris and the inner surface of the trabecular mesh work through which the aqueous humor is normally reabsorbed. Closure of this anatomical angle prevents normal drainage of aqueous humor from the anterior chamber of the eye.

In open angle glaucoma (syn. "chronic simple glaucoma" "simple glaucoma", "wide-angle glaucoma) the angle of the anterior chamber remains normal, but the drainage of aqueous humor from the anterior chamber is impeded or blocked by other means, such as edema or swelling of the trabecular spaces, abnormal pigment dispersion, or non-perforating injury to the eye resulting in vascular congestion.

Various pharmacologic modes of treatment have been used to lessen the intraocular fluid pressure in glaucoma patients. Drugs which have been administered to treat glaucoma have included parasympathomimetic agents of the choline ester type (e.g., bethanechol, carbachol and methacholine), carbonic anhydrase inhibitors (e.g., acetazolamide), anticholinesterase agents (e.g., physostigmine, pilocarpine, demecarium, echothiophate and isoflurophate), sympathomimetic agents (e.g, epinephrine, phenylephrine) and β-adrenergic blocking agents (e.g., tymolol). However, these various drug therapies for glaucoma are sometimes associated with significant untoward effects, including headache, blurred vision, allergic reactions, retinal detachment, phacodinesis, histological changes within the eye and potential interactions with other drugs.

As an alternative to pharmacologic modes of therapy, at least some glaucoma patients may be treated surgically by creating surgical openings into the anterior chamber of the eye, to facilitate drainage of excess aqueous humor from the anterior chamber. Many of these surgical techniques involve the formation of an opening or hole into the anterior chamber, under the conjunctiva and/or scleral flap such that fluid will be drained by filtration from the anterior chamber of the eye, into the tissues located within the lateral wall of the eye. The major problems associated with these surgical filtration procedures stem from the size of the opening or hole made into the anterior chamber. These problems include hypotony, synechiae, inflammation, cataract, corneal decompensation (edema), vitritis, choroidal separation (detachment), macular edema, and infections which may cause endophthalmitis. Moreover, such glaucoma filtration surgery is often unsuccessful due to the formation of dense fibrovascular connective tissue (e.g., scar tissue) around the surgical opening formed into the anterior chamber. Such proliferation of connective tissue tends to close off the surgically-formed opening into the anterior chamber, thereby deterring or preventing the desired filtration of aqueous humor into the subconjunctival space.

In view of post-surgical complications associated with the development of fibrovascular connective tissue (e.g., scar tissue) around the surgical site, a number of implantable drainage devices have been used to ensure that the desired filtration and outflow of aqueous humor through the surgically-formed opening will continue, despite the formations of, scar tissue during the post operative period. Examples of implantable shunts or other implantable apparatus which have previously been implanted into the eye for drainage of aqueous humor from the anterior chamber of the eye include those described in U.S. Pat. Nos. 4,750,901 (Molteno), 5,041,081 (Odrich), 5,476,445 (Baerveldt), 4,886,488 (White), 5,454,796 (Krupin), 5,397,300 (Baerveldt), 5,372,577 (Ungerleider), 5,338,291 (Speckman, et al.), 5,300,020 (L'Esperance), 5,178,604 (Baerveldt, et al.), 5,171,213 (Price), 5,092,837 (Klein et al.), 4,968,296 (Klein et al.), 4,946,436 (Smith), 4,936,825 (Ungerleider), 4,886,488 (White), 4,806,382 (Burns et al.), 4,554,918 (White), 4,521,210 (Wong), 4,428,746 (Mendez), 4,184,491 (McGannon), 4,157,718 (Baehr), 4,030,480 (Meyer), 5,433,701 (Rubinstein), 5,346,464 (Camras), 5,073,163 (Lippman), 4,604,087 (Joseph), 5,180,362 (Worst), 5,520,631 (Li et al.).

The major disadvantage associated with the use of implantable shunts for treatment of glaucoma is that, in the immediate post operative period, the shunt may facilitate excessive fluid drainage which results in hypotony within the anterior chamber, flattening of the anterior chamber and potential choroidal detachment and/or phthisis bulbi. Such excessive post-operative fluid outflow may also result in expansion of the fibrous capsule located beneath the rectus muscles of the eye. Such expansion of the fibrous capsule can stretch and tighten the rectus muscles, thereby inducing heterotropia and impairing the motility of the eye in the quadrant wherein the implant is located. Additionally, due to the size of some of these shunt devices, the bulky presence of the device itself within the subconjunctival space can cause scleral erosion, changes in the natural curvature of the eye, or damage to adjacent vasculature and tissue. Other problems associated with the use of implantable shunt devices for the treatment of glaucoma involve friction and wear imparted by the implanted shunt device, irritation of the iris endothelium caused by insertion of the shunt device into the anterior chamber, and migration of microbes, cells, proteins or other matter through the lumen of the shunt device and into the anterior chamber of the eye.

ii. Hydrocephalus

Another disorder in which the build-up of abnormal fluid pressure is a hallmark is hydrocephalus. In hydrocephalus, excessive amounts of cerebrospinal fluids accumulate within skull, generally resulting in elevated intracranial pressure. The chronic elevation in intracranial pressure caused by such excessive cerebrospinal fluid within the skull typically results in enlargement of the head, prominence of the forehead, brain atrophy, mental deterioration, and convulsions. Hydrocephalus is maybe of congenital origin or may be an acquired disease. In some patients, hydrocephalus is of sudden onset while in others it is slowly progressive.

In addition to various pharmacologic therapies, the surgical approach to treatment of hydrocephalus often involves the implantation of a shunt which facilitates drainage of excess cerebrospinal fluid from the intracranial space, to other areas of the body wherein it can be tolerated—most often into the peritoneal cavity.

In addition to glaucoma and hydrocephalus, numerous other diseases and disorders involve the buildup of excessive fluid within one or more anatomical spaces (i.e., cavities) of the body, and may be effectively treated by shunting of the excessive fluid from the affected body space (i.e., body cavity) to other region(s) of the body. However, in many cases, it is desirable that an implantable shunt device be used, and that such shunt device be valved or pressure-regulated such that only excessive fluid will be removed from the affected body cavity, while allowing the normal amount of such fluid to remain within the affected body cavity, so long as the pressure within the cavity is in the normal range. Thus, it is desirable for the implanted shunt device to include a pressure-sensitive opening or other pressure-actuated valving apparatus which will allow fluid to flow out of the affected body cavity only when the fluid within the body cavity has exceeded a predetermined maximum pressure.

One complication associated with the use of implantable shunt devices to drain fluid from body cavities is that proteins, cellular matter, or other debris may block the lumen of the shunt tube thereby interfering with the drainage of fluid through the tube. Also, proliferation of tissue or blebs may compress, collapse, or block the shunt tube. Moreover, pathogenic microorganism or irritating proteins or other matter may migrate through the lumen of the shunt tube into the affected body cavity in a manner which can lead to iatrogenic infection, irritation or inflammation of the affected body cavity.

Given the above-summarized limitations and drawbacks associated with the implantable fluid-shunting devices of the prior art, it is apparent that no single fluid-shunting device has proven to be optimal for all applications. Accordingly, there exists a need in the art for the development for new implantable fluid-shunting devices which include: a) means for valving or pressure-regulation of the fluid outflow and b) means for preventing microbes, proteins, cells or other matter from clogging the shunt or migrating through the shunt into the affected body cavity.

SUMMARY OF THE INVENTION

The present invention provides implantable devices for shunting or draining fluid from one intracorporeal location to another. In general, the implantable devices of the present invention comprise an elongate tube having a lumen extending longitudinally therethrough and a diffusion chamber mounted on the proximal end of the tube. The distal end of the tube is open, while the proximal end of the tube is closed. A pressure-openable aperture is formed in a proximal portion of the tube which extends into the interior of the diffusion chamber. Such pressure-openable aperture will open when the pressure of fluid within the lumen of the tube exceeds a predetermined maximum pressure. In this manner, fluid will be permitted to flow from the distal end of the tube, through the lumen of the tube, through the pressure-openable aperture and into the interior of the diffusion chamber. Thereafter, such fluid may diffuse outwardly through the diffusion chamber and into the surrounding tissues or spaces of the body. The diffusion chamber is preferably formed of material which will prevent unwanted matter (e.g., proteins, solid particles greater than a predetermined size, or host cellular matter, such as tissues or individual cells), from entering the interior of the diffusion chamber and (a) interfering with the desired opening and closing of the pressure-openable aperture or (b) migrating through the lumen of the tube and into the region of the body adjacent the distal end of the tube.

The implantable devices of the present invention may be utilized for numerous fluid-shunting applications including the treatment of glaucoma wherein aqueous humor is shunted from the anterior chamber of the eye, and the treatment of hydrocephalus, wherein cerebrospinal fluid is shunted from the intracranial space into another body cavity (e.g., the peritoneal cavity).

Further objects and advantages of the present invention will become apparent to those skilled in the art upon reading and understanding the following detailed description and the accompanying drawings.

DETAILED DESCRIPTION OF THE PREFERRED EMBODIMENTS

The following detailed description, and the accompanying drawings to which it refers are provided for purposes of exemplifying and illustrating representative examples and embodiments of the invention only, and are not intended to limit the scope of the invention in any way. Indeed, no effort has been made to exhaustively illustrate and describe all possible embodiments and configurations in which the present invention may take physical form.

i. Construction and Configuration of the Fluid Shunting Device

With reference to FIGS. 1–4, there is shown a first embodiment of an implantable fluid shunting device 10 comprising an elongate tube 12 having a lumen 14 extending longitudinally therethrough and a diffusion chamber 20 mounted on the proximal end thereof. The tube 12 has an open distal end 16, a closed proximal end 18 and a pressure openable aperture 30 which is located in a proximal portion PP of the tube 12 which extends into the interior of the diffusion chamber 20.

In this regard, the diffusion chamber 20 is mounted on the tube 12 such that the proximal portion PP of the tube 12 adjacent the proximal end 18 thereof, extends into the inner cavity 26 of the diffusion chamber 20. The diffusion chamber 20 is mounted in sealing contact upon the outer surface of the tube 12 such that fluid which flows out of the tube 12 into the inner cavity 26 of the diffusion chamber 20 will not freely leak therefrom. The diffusion chamber 20 is preferably formed of membranous material (e.g., permeable or semipermeable membrane material) which will permit the fluid which is desired to be drained by the tube 12 to flow from the inner cavity 26 of the diffusion chamber, outwardly and into the region of the body wherein the diffusion chamber 20 is positioned, while preventing predetermined types of unwanted matter (e.g., proteins, solid particles which are greater than a predetermined size, etc.) from passing inwardly through such membrane and into the inner cavity 26 of the diffusion chamber 20. Additionally, the material of the diffusion chamber 20 will prevent host cellular matter (e.g., tissues or cells such as fibroblasts, endothelium, epithelium, blood cells) from invading (e.g., ingrowing or migrating) the outer surface or inner lumen of the tube 12 and/or the inner cavity 26 of the diffusion chamber 20.

Figures 1, 2, 3:
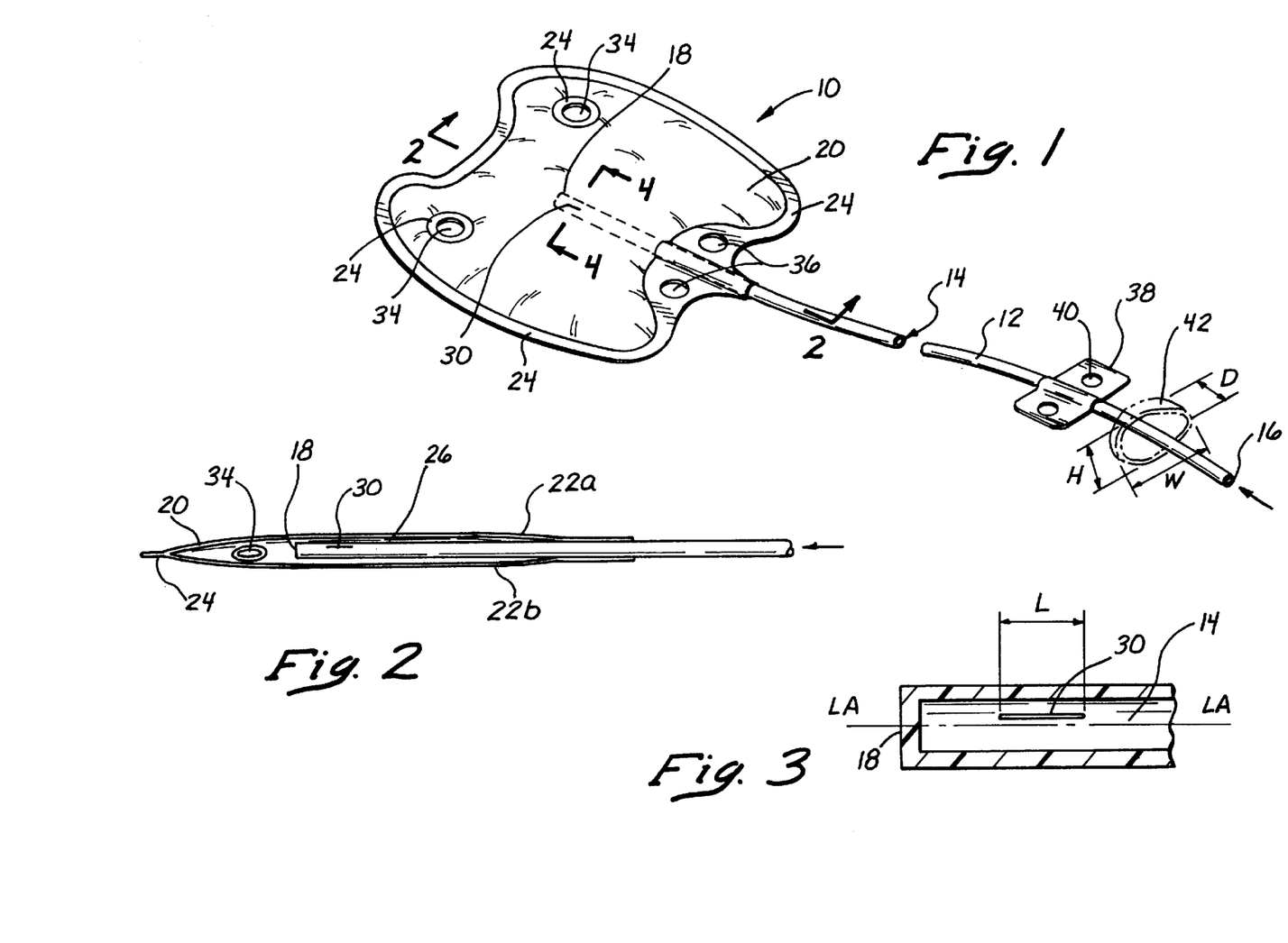
FIG. 1 is a perspective view of one embodiment of an implantable fluid-shunting device of the present invention.
FIG. 2 is a longitudinal sectional view through line 2—2 of FIG. 1.
FIG. 3 is an enlarged longitudinal sectional view of the proximal-most portion of the fluid-carrying tube component of the device of FIG. 1.

In the particular embodiment shown in FIGS. 1–3, diffusion chamber 20 is constructed of an upper membrane wall 22a and lower membrane wall 22b. The upper and lower membrane walls 22a, 22b are sealed to one another at their edges to form a sealed perimeter flange 24. Such sealing of the upper and lower membrane walls 22a, 22b also forms a fluid-tight seal with the tube 12, while allowing the proximal portion PP of the tube 12 to extend into the inner cavity 26 of the diffusion chamber 22.

In the embodiment shown in FIGS. 1–3, suture passage apertures 36 are formed in the diffusion chamber 20 to facilitate suturing of the device 10 at it's desired position within the body. Also, tissue ingrowth apertures 34 are formed in the diffusion chamber such that tissue may grow through such apertures 34, thereby firmly anchoring the diffusion chamber 20 in a substantially fixed position within the surgically-created pocket in which it is implanted.

Also in the embodiment of FIGS. 1–3, an optional suture tab 38 having suture passing apertures 40 is affixed to the outer surface of the tube 12, at a spaced distance proximal to the distal end 16 of the tube 12 to further facilitate suturing of the tube 12 in a desired position within the body.

Also in the embodiment of FIGS. 1–3, an optional concave abutment flange 42 is formed on the outer surface of the tube 12 to facilitate and maintain proper positioning of the tube 12 when implanted within the body in the glaucoma-treatment application described in detail herebelow. It will be appreciated that, although the embodiment shown uses a concave abutment flange 42, such abutment flange 42 may be of numerous different configurations to facilitate and maintain the desired positioning of the tube 12 in various other anatomical structures and locations of the body.

Figure 5:
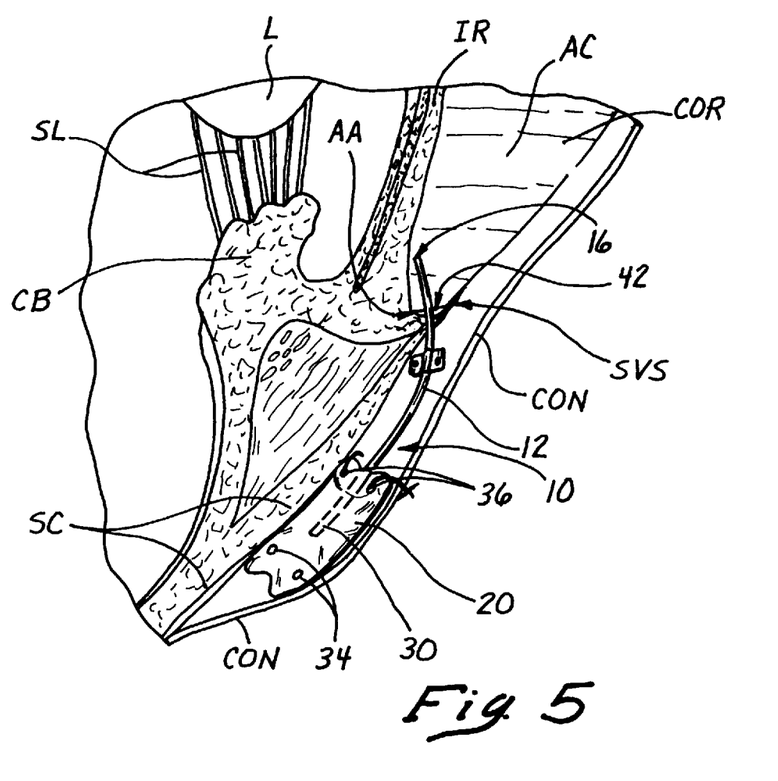
FIG. 5 is partial transverse sectional view through a portion of a human eye showing an implantable fluid shunting device of the present invention positioned therewithin to relieve excessive pressure within the anterior chamber of the eye.

The particular details and sizing of this concave abutment flange 42 in connection with a particular application of the invention for the treatment of glaucoma is described in more detail herebelow, and shown in FIG. 5. In many glaucoma treatment applications, it will be desirable for such concave abutment flange 42 to have a width W of approximately 3 mm, a depth D of approximately 1 mm, and a height H of approximately 1 mm.

The pressure-openable aperture 30 may specifically comprise a slit aperture 30 as shown in the drawings. Such slit aperture 30 is formed in the wall of the proximal portion PP of the tube 12, to facilitate outflow of fluid from the lumen 14 of the tube 12 into the inner chamber 26 of diffusion chamber 20. This pressure-openable slit aperture 30 is biased to a closed configuration whereby the opposite sides of the slit aperture 30 are in sealing contact with one another to prevent fluid from flowing from the lumen 14 of the tube 12 into the inner cavity 26 of the diffusion chamber 20 so long as the fluid pressure within the lumen 14 of the tube 12 is below a predetermined maximum pressure $P_{MAX}$. However, the pressure-openable slit aperture 30 is configured and constructed so as to spread apart (i.e., open) when the fluid pressure within the lumen 14 of the tube 12 exceeds such predetermined maximum pressure $P_{MAX}$, thereby allowing fluid to flow from the lumen 14 of tube 12 into the inner cavity 26 of the diffusion chamber 20 until the fluid pressure within the lumen 14 of the tube 12 falls below a predetermined aperture closing pressure $P_{CLS}$, at which time the biasing of the pressure-openable slit aperture 30 will cause such slit aperture 30 to once again assume its closed configuration. The predetermined maximum pressure $P_{MAX}$ and the predetermined aperture closing pressure $P_{CLS}$ will be determined on the basis of the intended application of the device 10, to facilitate drainage of fluid from a body cavity wherein the open distal end 16 of the tube 12 is located, into the diffusion chamber 10 when such pressure exceeds the predetermined maximum pressure $P_{MAX}$, but to prevent such fluid pressure within the body cavity from falling below the predetermined closing pressure $P_{CLS}$ so as not to inadvertently drain too much of such fluid from the body cavity. In this manner, the amount of fluid left within the affected body cavity should be sufficient to perform the intended physiological functioning of the fluid (if any), but such fluid will be prevented by the device 10 from over-accumulating within the body cavity in a manner which creates excessive or non-physiological pressure within the body cavity.

The specific size, shape, orientation and formation of the pressure-openable slit aperture 30 may vary, depending upon the desired predetermined maximum pressure $P_{MAX}$ and predetermined closing pressure $P_{CLS}$. In the particular embodiment shown, the predetermined maximum pressure $P_{MAX}$ which will cause the pressure-openable slit aperture 30 to open is a function of the thickness T of the wall of the tube, the width or thickness of the tool utilized to make the pressure-openable slit aperture 30 in the wall of the tube 12, and the angle A of such slit aperture 30 relative to a radial line or ray R which is projectible at 90° to the longitudinal axis LA of the tube 12. When the tool or instrument utilized to make the pressure-openable slit aperture 30 is of minimal width so as not to create a slit which is incapable of assuming a fully closed configuration, the factors which will determine the predetermined maximum pressure $P_{MAX}$ at which the pressure-openable slit aperture 30 will open are a) the wall thickness T of the tube 12, b) the angle A of the slit aperture 30 relative to the transverse axis (e.g., radius line R) of the tube 12, c) the length L of the slit aperture 30, and d) the internal diameter ID of the tube.

Figure 4:
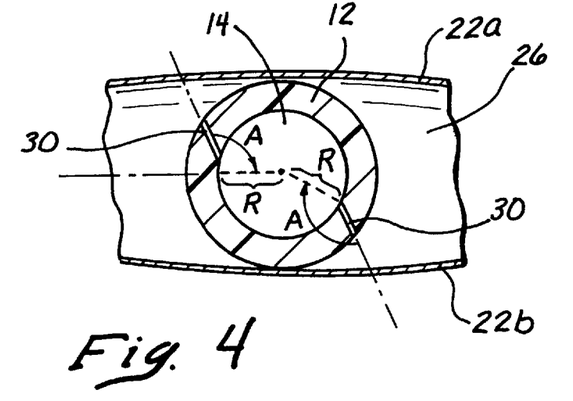
FIG. 4 is a cross-sectional view through line 4—4 of FIG. 1.

With respect to the angle A of the slit aperture 30 relative to the radial line or ray R of the tube, it is to be appreciated that in embodiments such as that shown in FIG. 4 wherein the lumen 14 of the tube 12 is round, the slit aperture 30 will form angle A relative to a radius line R which is projected from the inner end of the slit aperture 30 to the centerpoint of the round lumen 14. However, various alternative configurations may be employed wherein the lumen 14 of the tube is other than round, and in such alternative configurations the angle A of the slit aperture 30 will be defined relative to a transverse axis projected from the inner end of the slit aperture 30 to a centerpoint or center-of-flow point within the lumen 14 of the tube 12. In either instance, the angle A of the slit aperture 30 relative to such radial line or ray R will determine the amount of tube material which the slit aperture 30 must penetrate through, thereby determining at least in part the amount of fluid pressure which will be required to spread apart the adjacent sides of the slit aperture 30 to cause opening of the slit aperture 30. For example, with reference to the showing of FIG. 4, if the slit aperture 30 were to extend straight through the wall of the tube 12, the angle A would be 180°, and the slit aperture 30 would pass through the minimum amount of tubular material determined by the wall thickness of the tube 12. However, as the angle A decreases from 180° to 90°, the amount of tubular material through which the slit aperture 30 must pass will increase, thereby requiring greater pressure to part the opposite sides of the slit aperture 30 to accomplish opening thereof. Thus, it is in this manner that the angle A of the slit aperture 30 relative to the radial line or ray R of the tube 12 will function as one of the variables which are determinative of the predetermined maximum pressure $P_{MAX}$ and/or the predetermined closing pressure $P_{CLS}$ of the slit aperture 30.

It will be appreciated that the tube 12 and diffusion chamber 20 may be formed of any material which is suitable for the particular application for which the device 10 is to be used. Examples of materials of which the tube 12 may be formed include, but are not necessarily limited to silicone, hydrogels, polyurethanes, polyesters, latex, natural rubbers, and, cellulosics. Examples of the materials of which the diffusion chamber may be formed include, but are not necessarily limited to, cellulose acetate, cellulosics, polyesters, polyfluorocarbons, hydrogels, polyolefins, a hydrogel made from at least one hydrophilic monomer and at least one olefinic/polyolefinic cross-linker, and, other natural polymers.

ii. Application of the Invention for Glaucoma Treatment

FIG. 5 shows the device of FIG. 1, implanted within the human eye for treatment of glaucoma. the anatomical structures shown in FIG. 5 are labeled in accordance with the following:

| | |
|---|---|
| Anterior Angle | AA |
| Anterior Chamber | AC |
| Ciliary Body | CB |
| Conjunctiva | CON |
| Cornea | COR |

-continued

| | |
|---|---|
| Iris | IR |
| Lens | L |
| Sclera | SC |
| Sinus Venosus Sclerae | SVS |
| Suspensory Ligaments | SL |

In this application of the device the tube 12 will typically have an outer diameter of approximately 0.6 mm, an inner diameter of approximately 0.3 mm and a length of approximately 40–45 mm. The concave abutment flange 42 will be positioned approximately 5 mm from the distal end 16 of the tube 12, and will have a height H of approximately 1mm, a width W of approximately 3 mm and a depth D of approximately 1 mm.

The shape of the concave abutment flange 42 may be other than circular, and preferably may be oval shape in the manner depicted in the figures. Such oval configuration of the concave abutment flange 42 will facilitate the desired passage of the flange 42 in a collapsed configuration through the opening formed into the anterior chamber AC of the eye, and will thereafter permit the fully deployed and uncollapsed flange 42 to properly seat or nest within the peripheral corner of the anterior chamber AC, in the manner shown in FIG. 5.

As shown, the diffusion chamber 20 and proximal portion of the tube 12 are implanted in a cavity formed between the conjunctiva CON and sclera SC, on the lateral aspect of the ocular bulb. The diffusion chamber 20 may be doubled over or folded to facilitate insertion through a relatively small incisions and may subsequently be opened or unfolded while in the surgically-created pocket of tissue formed between the conjunctiva CON and sclera SC. The distal end 16 of the tube is advanced through an opening formed in the sclera, inboard of the sinus venosus sclerae SVS. The concave abutment flange 42 is passed through the surgically formed opening in the sclera and is retracted so as to be in firm abutment with the sclera and/or adjacent tissue, thereby maintaining the tube 12 in its desired longitudinal position with the appropriate length of tube 12 extending into the anterior chamber AC. Suture tab 38 is secured to the adjacent tissue of the conjunctiva CON by way of sutures, thereby affixing the distal portion of the tube 12 in its desired position, and maintaining the concave abutment flange 42 in contact with the sclera and/or adjacent tissue as described hereabove.

If necessary or desirable, the diffusion chamber 20 of the device 10 may be initially secured within its desired implantation position by passing sutures through the suture-receiving apertures 36, as shown. Following implantation, tissue will ingrow through tissue ingrowth apertures 34 to further facilitate anchoring and attachment of the diffusion chamber 20 to the surrounding tissue of the conjunctiva CON and sclera SC. Thus, with the device 10 implanted within the eye in the manner shown in FIG. 5, excess aqueous humor in the anterior chamber AC will enter the open distal end 16 of the tube 12, and will flow through the lumen 14 of the tube 12. When the pressure of aqueous humor within the lumen 14 of the tube 12 exceeds the predetermined maximum pressure $P_{MAX}$ the pressure-openable slit aperture 30 will be caused to open, thereby allowing the access humor to flow out into the inner cavity 26 of the diffusion chamber 20. Such outflow of aqueous humor will continue until the pressure of aqueous humor within the lumen 14 of the tube 12 falls below the predetermined closing pressure $P_{CLS}$ of the pressure-openable slit aperture 30, at which time the pressure-openable slit aperture 30 will once again assume its closed configuration. Thereafter, the pressure-openable slit 30 will remain closed until such time as the pressure of aqueous humor within the lumen 14 of the tube 12 once again exceeds the predetermined maximum pressure $P_{MAX}$.

For many glaucoma patients, the desired predetermined maximum pressure $P_{MAX}$ will be 20 mm/Hg, and the desired closing pressure $P_{CLS}$ of the pressure-openable slit aperture 30 will be approximately 10 mm/Hg. As explained hereabove, the length and angular orientation of the pressure-openable slit apertures 30 will be adjusted to provide these desired predetermined maximum pressure $P_{MAX}$ and predetermined closing pressure $P_{CLS}$. In this regard, the pressure of aqueous humor within the anterior chamber AC of the eye will be prevented from exceeding the predetermined maximum pressure $P_{MAX}$ of approximately 20 mm/Hg, and will also be prevented from falling below the predetermined closing pressure $P_{CLS}$ of approximately 10 mm/Hg. Thus, in this application of the present invention, the device 10 will operate to maintain pressure of aqueous humor within the anterior chamber within the 10–20 mm/Hg range, and preferably in a range of approximately 10–15 mm/Hg.

Excess aqueous humor which has passed through the tube 12 and into the inner cavity 26 of the diffusion chamber 20 will subsequently diffuse outwardly through the membrane walls 22a, 22b of the chamber and into the surrounding tissue. Such fluid will, thereafter, be assimilated by normal physiological action of the tissues.

In this glaucoma-treatment application, it is preferable that the membrane walls 22a, 22b of the diffusion chamber 20 be formed of cellulose acetate and/or polyvinylidene acetate, as such materials exhibit desirable host tissue compatibility. This preferred membrane material will allow the aqueous humor which collects in the inner cavity 26 to diffuse outwardly therethrough, but will prevent cellular ingrowth, proteins or particulate matter from passing inwardly into the inner cavity 26 of the diffusion chamber 20 where such matter could a) block or interfere with the pressure-openable slit apertures 30 or b) migrate through the lumen 14 of the tube 12 into the anterior chamber AC of the eye.

Also, in this glaucoma-treatment application, it is preferable that the tube 12 be formed of silicone.

iii. Application of the Invention for Treatment of Hydrocephalus

Figure 6:
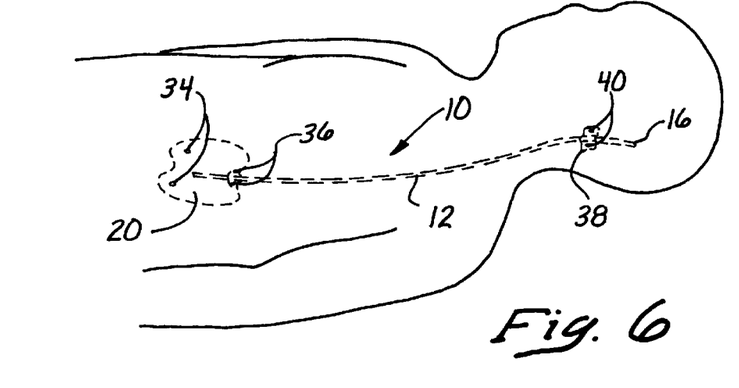
FIG. 6 is a schematic showing of a human body wherein an implantable fluid-shunting device of the present invention has been surgically installed to drain excessive cerebrospinal fluid from the brain to the peritoneal cavity.

FIG. 6 shows a variant of the device shown in FIGS. 1–3, implanted in the human body for treatment of hydrocephalus.

In this application of the device 10, the device 10 is devoid of the optional concave abutment flange 42. The device 10 is implanted such that the diffusion chamber 20 is positioned within the peritoneum, and the tube 12 is passed subcutaneously over the thorax, neck and into the base of the skull. The distal portion of the tube 12 may reside in the space between the brain and cranium, or may be inserted into a ventricle of the vein in accordance with the applicable treatment technique for the particular case of hydrocephalus being treated. The optional suture tab 38 may be employed to anchor the tube 12 in its desired position within the cranial vault. Also, the suture passage apertures 34, 36 formed on the diffusion chamber 20 may be utilized to suture the diffusion chamber 20 in its desired position within the patients abdomen.

When the device 10 has been implanted in the manner shown in FIG. 6, excess cerebrospinal fluid will enter the open distal end 16 of the tube 12 and will flow through the lumen 14 of the tube. When the cerebrospinal fluid pressure within the lumen 14 of the tube 12 exceeds the predetermined maximum pressure $P_{MAX}$, the pressure-openable slits 30 will open, thereby allowing the excess cerebrospinal fluid flow into the inner cavity 26 of the diffusion chamber 20. Such outflow of cerebrospinal fluid will continue until the pressure of cerebrospinal fluid within the lumen 14 of the tube 12 falls below the predetermined closing pressure $P_{CLS}$.

In many hydrocephalus patients, the desired predetermined maximum pressure $P_{MAX}$, for treatment of hydrocephalus will be in the range of 10–20 mm/Hg, and the desired predetermined closing pressure $P_{CLS}$ will be in the range of 0–10 mm/Hg. In this manner, the pressure of cerebrospinal fluid within the ventricle of the brain, or otherwise within the cranium, may be maintained in a prescribed range, such as a preferred range of 5–14 mm/Hg, in accordance with the particular predetermined $P_{MAX}$ and $P_{CLS}$ of the device 10.

iv. Alternative Configurations/Applications of the Invention

FIGS. 7a–7g show alternative embodiments of the device 10a–10g wherein the diffusion chamber 20a–20g is of varying configuration, to facilitate use of the device 10–10g in various other applications.

It will be appreciated that, the diffusive surface area of the diffusion chamber 20a–20g may be altered by changing the shape of the diffusion chamber 20–20g. Moreover, alterations or variations in the shape of the diffusion chamber 20–20g, especially those wherein openings or invaginations are formed in the diffusion chamber 20–20g, may form areas into which tissue may ingrow so as to soundly anchor and fix the diffusion chamber 20–20g within its desired implantation position. The utilization of indigenous tissue ingrowth as a means for physical fixation and anchoring of the diffusion chamber 20–20g is desirable in that it may eliminate the need for the use of permanent sutures for anchoring of the diffusion chamber 20–20g, as sutures may tend to exert physical stress or force upon the diffusion chamber 20–20g and/or adjacent tissue. Furthermore, promoting tissue ingrowth within specific regions of the diffusion chamber 20–20g may firmly anchor and hold the diffusion chamber 20–20g in its desired implantation position so as to deter or prevent post-surgical micromovement of the device 10. In this regard, the embodiments illustrated in FIGS. 7a–7g incorporate various modifications wherein multiple projections, invaginations, and other configurational variations are formed in the diffusion chamber 20a–20g.

Additionally, it will be appreciated that the shape of the diffusion chamber may be modified to facilitate a) folding of the diffusion chamber to facilitate its insertion into a specific area of the body and b) ease of placement and retention of the diffusion chamber 20a–20g at its intended site of implantation.

The alternative embodiments shown in FIGS. 7a–7g are merely examples of the multitude of shapes and configurations in which the diffusion chamber 20a–20g may be formed and, accordingly, the intended shape or configuration of the diffusion chamber 20 shall not be limited to only those shapes and configurations shown in the drawings, but shall include any and all other shapes or configurations in which the diffusion chamber 20 may be formed.

Figure 7A:
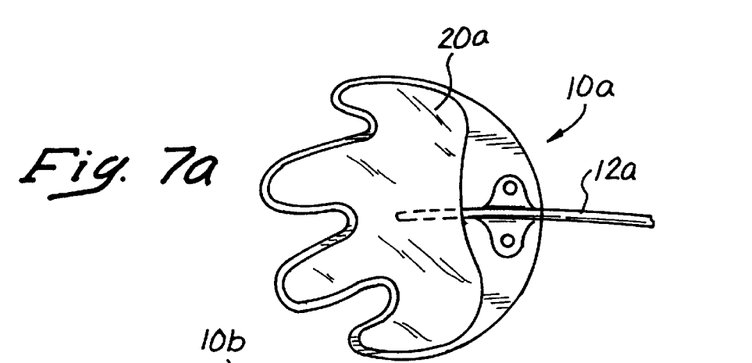
FIGS. 7a–7g are partial perspective views of alternative embodiments of the implantable fluid-shunting device of the present invention.
Figures 7B, 7C:
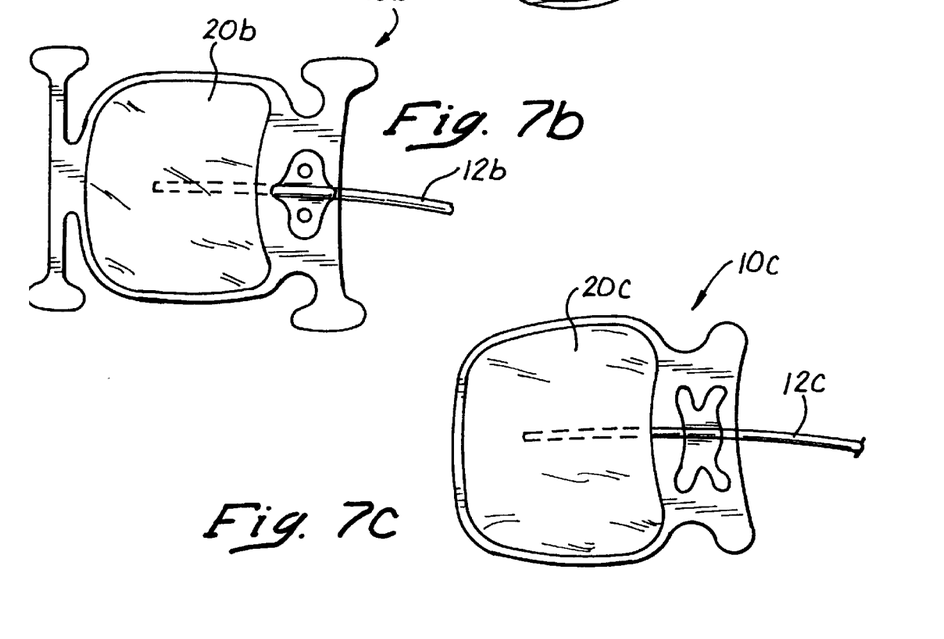
Figure 7D:
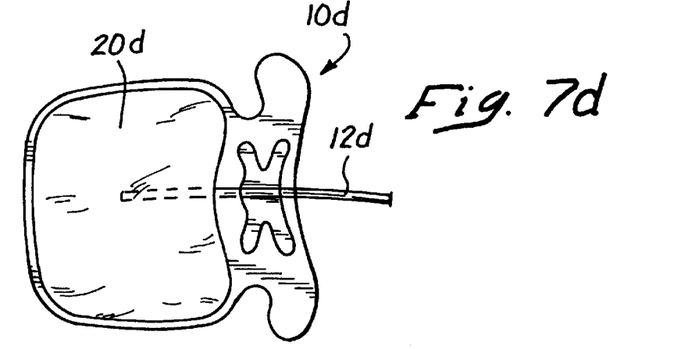
Figure 7E:
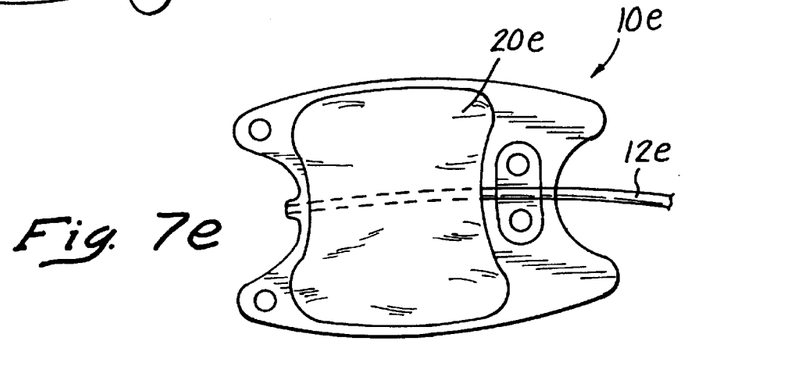
Figure 7F:
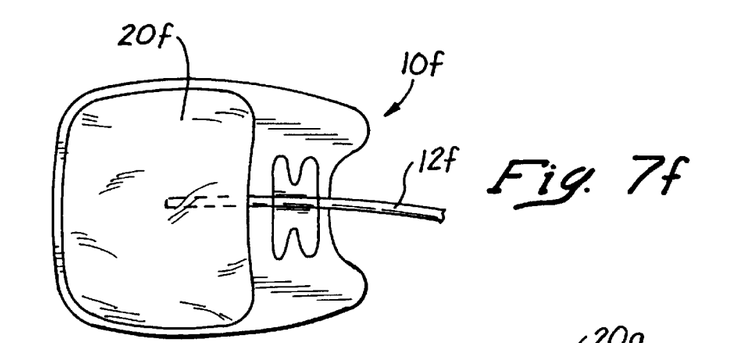
Figure 7G:
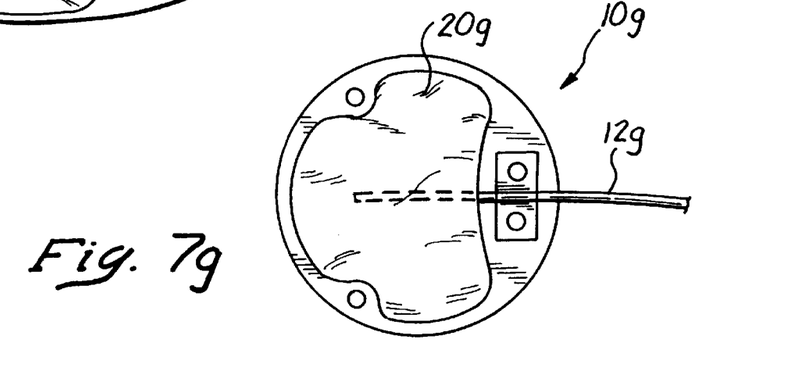

In particular, the diffusion chambers 20a, 20e, 20g shown in FIGS. 7a, 7e, and 7g, respectively, have curved or tapered outer edges whereby the proximal end of the diffusion chambers 20a, 20e, 20g is narrower than its distal end, thereby facilitating easy extraction and removal of the diffusion chamber 20a, 20e, 20g, if and when such removal is desired.

The invention has been described hereabove with reference to certain presently preferred embodiments, and no attempt has been made to describe all possible embodiments in which the invention may take physical form. Indeed, numerous modifications, additions, deletions and alterations may be made to the above-described embodiments without departing from the intended spirit and scope of the invention. Accordingly, it is intended that all such additions, deletions, modifications and alterations be included within the scope of the following claims.

What is claimed is:

1. A device which is implantable in a mammalian body to prevent fluid from exceeding a predetermined maximum pressure, within an anatomical cavity of the mammalian body, said device comprising:

a tube having a side wall, closed proximal end, a distal opening, and a hollow lumen extending longitudinally from said distal opening to said closed proximal end;

a diffusion chamber having an inner cavity defined therewithin, said diffusion chamber being formed of a material that allows fluid to diffuse outwardly therethrough but which prevents cellular ingrowth from invading the inner cavity of said diffusion chamber and mounted in fluid-tight sealing contact upon said tube such that a proximal portion of said tube, located adjacent the proximal end thereof, extends into the inner cavity of said diffusion chamber; and a pressure-openable aperture formed in the proximal portion of said tube that extends into the inner cavity of said diffusion chamber, said pressure-openable aperture being biased to a closed configuration, and being openable in response to fluid pressure exceeding said predetermined maximum pressure, within the lumen of said tube.

2. The device of claim 1 wherein said diffusion chamber comprises at least one membrane formed of material which will allow said fluid to diffuse out of the inner cavity of said diffusion chamber, while preventing predetermined types of matter from passing through said membrane into the inner cavity of said diffusion chamber.

3. The device of claim 2 wherein said membrane is a permeable membrane.

4. The device of claim 2 wherein said membrane is a semipermeable membrane.

5. The device of claim 4 wherein said predetermined types of matter which said membrane will prevent from passing into said diffusion chamber are selected from the group of matter types consisting of:

a) microbes;

b) proteins;

c) particles exceeding 5 microns in size; and, d) host cellular matter.

6. The device of claim 4 wherein said diffusion chamber comprises material which will allow said fluid to diffuse out of the inner cavity of the diffusion chamber, but will prevent host cellular matter from entering the inner cavity of the diffusion chamber.

7. The device of claim 1 wherein said diffusion chamber is formed at least partially of materials selected from the group of materials consisting of:

cellulose acetate;

cellulosics;

polyesters;

polyfluorocarbons;

polyvinylidene fluoride;

hydrogels;

polyolefins;

a hydrogel made from at least one hydrophilic monomer and at least one olefinic/polyolefinic cross-linker; and, other natural polymers.

8. The device of claim 1 wherein said tubing is formed at least partially from material selected from the group of materials consisting of:

silicone;

hydrogels;

polyurethanes;

polyesters;

latex;

natural rubbers; and, cellulosics.

9. The device of claim 1 wherein said diffusion chamber comprises:

an upper membrane wall having at least one peripheral edge; and, a lower membrane wall having at least one peripheral edge;

said upper and lower membrane walls being fused to one another about their peripheral edges to form said diffusion chamber.

10. The device of claim 1 wherein said pressure-openable aperture comprises an elongate slit.

11. The device of claim 10 wherein said elongate slit is formed in said tube such that said elongate slit is substantially parallel to the longitudinal axis of the tube.

12. The device of claim 11 wherein said tube has a radius, and wherein said elongate slit extends through the wall of said tube at an angle relative to the radius of which has been predetermined to cause said slit to open when a desired maximum pressure $P_{MAX}$ of fluid is present within the lumen of the tube.

13. A method for preventing predetermined types of undesired matter from interfering with the functioning of a tubular shunt which has been implanted in a mammalian body such that a distal end of the tubular shunt is positioned in an anatomical cavity and a proximal end of the shunt located in another region of the body, such that fluid from the anatomical cavity will be drained by the tubular shunt to the other region of the body, said method comprising the step of:

forming a diffusion barrier about the proximal end of the tubular shunt, said diffusion barrier being formed of material which will allow fluid flowing out of the proximal end of said tubular shunt and to subsequently diffuse through said diffusion barrier and into said other region of the body, while preventing said predetermined type of undesirable matter from passing from said other region of the body, into said tubular shunt.

14. The method of claim 13 wherein the diffusion barrier form about the proximal end of the tubular shunt in accordance with the method, is a diffusion chamber having an inner cavity formed therewithin, said diffusion chamber being mounted upon said tubular shunt such that a proximal portion of said tubular shunt, adjacent the proximal end thereof, extends into the inner cavity of said diffusion chamber.

* * * * *